United States Patent
Causey, III et al.

(10) Patent No.: US 6,248,067 B1
(45) Date of Patent: Jun. 19, 2001

(54) ANALYTE SENSOR AND HOLTER-TYPE MONITOR SYSTEM AND METHOD OF USING THE SAME

(75) Inventors: James D. Causey, III; Paul H. Kovelman, both of Simi Valley; Richard E. Purvis, Pasadena; John J. Mastrototaro, Los Angeles, all of CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/246,661

(22) Filed: Feb. 5, 1999

(51) Int. Cl.[7] ........................................... A61B 5/00
(52) U.S. Cl. ........................ 600/365; 600/347; 128/903
(58) Field of Search ........................... 600/300, 301, 600/309, 310, 316, 322, 345, 347, 364, 365; 128/903, 904

(56) References Cited

U.S. PATENT DOCUMENTS

| | | | |
|---|---|---|---|
| 4,494,950 | * 1/1985 | Fischell | 128/903 |
| 5,417,222 | 5/1995 | Dempsey et al. | |
| 5,507,288 | 4/1996 | Bocker et al. | |
| 5,569,186 | 10/1996 | Lord et al. | 604/67 |
| 5,665,065 | 9/1997 | Colman et al. | 604/66 |
| 5,701,894 | * 12/1997 | Cherry et al. | 600/300 |
| 6,103,033 | 8/2000 | Say et al. | 156/73.1 |
| 6,134,461 | 10/2000 | Say et al. | 600/345 |

FOREIGN PATENT DOCUMENTS

| | | |
|---|---|---|
| 0880936 | 12/1998 | (EP) . |
| 9401039 | 1/1994 | (WO) . |
| 9956613 | 11/1999 | (WO) . |

OTHER PUBLICATIONS

T. Arai, et al., "A Portable Transcutaneous Blood Glucose Monitoring System Using Non–Invasive Collection of Suction Effusion Fluid from Skin", *IEEE*, pp. 812–813 (1994).

* cited by examiner

*Primary Examiner*—Eric F. Winakur
(74) *Attorney, Agent, or Firm*—MiniMed Inc.

(57) ABSTRACT

A Holter-type monitor system includes a remotely located data receiving device, an analyte sensor for producing signal indicative of a characteristic of a user, and a Holter-type recording device. The Holter-type recording device includes a housing, a sensor connector, a processor, and a data port. The sensor connector receives the produced signals from the analyte sensor. The processor is coupled to the sensor connector and stores the signals from the analyte sensor for delivery to the remotely located data receiving device. The recording device is coupled to the processor for downloading the stored signals to the remotely located data receiving device. The data receiving device may be a characteristic monitor, a data receiver that provides data to another device, an RF programmer, a medication delivery device (such as an infusion pump), or the like.

41 Claims, 4 Drawing Sheets

ANALYTE SENSOR AND HOLTER-TYPE MONITOR SYSTEM AND METHOD OF USING THE SAME

FIELD OF THE INVENTION

This invention relates to Holter-type monitor systems and, in particular embodiments, to devices and methods for Holter-type monitoring of an analyte sensor to determine a characteristic of a body.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571. However, the monitors for these continuous sensors provide alarms, updates, trend information and require sophisticated hardware to allow the user to program the monitor, calibrate the sensor, enter data and view data in the monitor and to provide realtime feedback to the user. This sophisticated hardware makes it most practical for users that require continuous monitoring with feedback to maintain tight control over their conditions. In addition, these systems require the user to be trained in their use, even if to be worn for short periods of time to collect medical data which will be analyzed later by a doctor.

Doctors often need continuous measurements of a body parameter over a period of time to make an accurate diagnosis of a condition. For instance, Holter monitor systems are used to measure the EKG of a patient's heart over a period of time to detect abnormalities in the heart beat of the patient. Abnormalities detected in this manner may detect heart disease that would otherwise go undetected. These tests, while very useful are limited to monitoring of bio-mechanical physical changes in the body, such as a heart beat, respiration rate, blood pressure or the like.

SUMMARY OF THE DISCLOSURE

It is an object of an embodiment of the present invention to provide an improved Holter-type monitor system with an analyte sensor set and monitor connection device, which obviates for practical purposes, the above mentioned limitations.

According to an embodiment of the invention, a Holter-type monitor system includes a remotely located data receiving device, an analyte sensor for producing signal indicative of a characteristic of a user, and a Holter-type recording device. In preferred embodiments, the Holter-type recording device includes a housing, a sensor connector, a processor, and a data port. The sensor connector receives the produced signals from the analyte sensor. The processor is coupled to the sensor connector and stores the signals from the analyte sensor for delivery to the remotely located data receiving device. The download data port of the Holter-type recording device is coupled to the processor for downloading the stored signals to the remotely located data receiving device through the data port. In preferred embodiments, the data receiving device is a characteristic monitor. However, in other embodiments, the data receiving device is a data receiver that provides data to another device, an RF programmer, a medication delivery device (such as an infusion pump), or the like. In particular embodiments, the data port of the Holter-type recording device downloads the stored signals by radio frequencies, infrared emissions, or the like. Additional embodiments may include data storage memory and interface controls.

In particular embodiments, the analyte sensor is an implantable, percutaneous or skin surface analyte sensor, and the sensor connector of the Holter-type recording device includes a cable that is connected to the implantable, percutaneous or skin surface analyte sensor. Also, the analyte sensor can be configured for a wired connection to a characteristic monitor, and the sensor connector of the Holter-type recording device is formed to connect to the configured analyte sensor. Still further embodiments of the Holter-type recording device include a receiver to receive data and instructions from the remotely located data receiving device, or the like.

Embodiments of the Holter-type recording device may include a bio-compatible adhesive to secure the housing to a skin surface of the user. Preferably, the housing of the Holter-type recording device is less than about 1.5 inches in diameter by 0.25 inches thick. In addition, the housing is resistant to fluids when immersed in a fluid, and operable in a temperature range of 0° C. to 50° C. The Holter-type recording device may also include a power source that has an operable life of at least 2 weeks.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

As shown in the drawings for purposes of illustration, the invention is embodied in a Holter-type monitor system coupled to a subcutaneous implantable analyte sensor set to provide continuous data recording of the sensor readings for a period of time. The recorded data then being later downloaded to another data processing device to determine body characteristic data over a period of time. In preferred embodiments of the present invention, the analyte sensor set and Holter-type monitor system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the Holter-type monitor system may also include the capability to be programmed to take data at specified time intervals or calibrated using an initial data input received from an external device. The Holter-type monitor system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may record sensor readings on an intermittent or continuous basis.

The Holter-type monitor system 1, in accordance with a preferred embodiment of the present invention includes a subcutaneous analyte sensor set 10, and a Holter-type recorder 100. The subcutaneous analyte sensor set 10 utilizes an electrode-type sensor, as described in more detail below. However, in alternative embodiments, the analyte sensor set may use other types of sensors, such as chemical based, optical based or the like. In further alternative embodiments, the sensors may be of a type that is used on the external surface of the skin or placed below the skin layer of the user. Preferred embodiments of a surface mounted analyte sensor would utilize interstitial fluid harvested from the skin.

The Holter-type recorder 100 generally includes the capability to record and store data as it is received from the analyte sensor 10, and then includes either a data port or wireless transmitter for downloading the data to a data processor 200, computer, communication station, or the like for later analysis and review. However, in alternative embodiments, the Holter-type recorder 100 may include a receiver, bi-directional data port, or the like, to facilitate two-way access between the Holter-type recorder 100 and a data processor 200, computer, communication station, or the like, for initial calibration and test of the analyte sensor set 10. The data processor 200, computer, or the like, utilizes the recorded data from the Holter-type recorder 100 to determine the characteristic history. Still further embodiments of the Holter-type recorder 100 have and use an input port for direct (e.g., wired) connection to a programming or data readout device and/or be used for calibration of the analyte sensor set 10. Preferably, any port would be water proof (or water resistant) or include a water proof removable cover. The Holter-type recorder can transmit the data by wire, or wireless signals including infrared frequencies, optical frequencies, audio frequencies, hyper-audio frequencies, ultrasonic frequencies, RF frequencies, or the like.

The purpose of the Holter-type monitor system 1 is to provide for better data recording and testing for various patient conditions utilizing continuous or near continuous data recording. In alternative embodiments, the data recording may be on an intermittent basis with the data being collected at predetermined periods of time ranging from minutes to hours. In addition, it is desired to utilize a relatively simple and inexpensive recording device that does not require patient interaction and is easily suited to just record sensor data. This obviates the need for an elaborate monitoring device.

The Holter-type monitor system 1 also removes inconvenience by separating the complicated monitoring process electronics into two separate devices; a Holter-type recorder 100, which attaches to the analyte sensor set 10; and a data processor 200, computer, communication station, or the like, which contains the software and programming instructions to download and evaluate data recorded by the Holter-type recorder 100. This provides several advantages over wire connected devices. For instance, the user can more easily conceal the presence of the monitor system 1, since a wire will not be visible (or cumbersome), with clothing. In addition, the use of multiple components (e.g., recorder 100 and data processor 200, computer, communication station, or the like) facilitates upgrades or replacements, since one module, or the other, can be modified or replaced without requiring complete replacement of the monitor system 1. Further, the use of multiple components can improve the economics of manufacturing, since some components may require replacement on a more frequent basis, sizing requirements may be different for each module, there may be different assembly environment requirements, and modifications can be made without affecting the other components.

The Holter-type recorder 100 takes raw analyte sensor data, such as glucose data or the like, from the subcutaneous analyte sensor set 10 and stores it for later download to the data processor 200, computer, communication station, or the like, which analyzes, displays and logs the received glucose readings. Downloaded data can be subjected to further detailed data analysis. In further embodiments, the Holter-type monitor system 1 may be used in a hospital environment or the like. Still further embodiments of the present invention may include one or more buttons on the Holter-type recorder 100 to record data and events for later analysis, correlation, or the like. In addition, the Holter-type recorder may include an on/off button for compliance with safety standards and regulations to temporarily suspend transmissions or recording. Further buttons could include a sensor on/off button to conserve power and to assist in initializing the analyte sensor set 10. The Holter-type recorder 100 may also be combined with other medical devices to combine other patient data through a common data network and telemetry system. The system may also include a separate glucose detection device (such as a meter or monitor) to provide calibration data for the data recorded by the Holter-type recorder 100. For instance, all downloaded data received by the processing device, computer, or the like, are post processed with the calibration data from the separate glucose detection device.

As shown in FIGS. 1–7, an implantable subcutaneous analyte sensor set 10 is provided for subcutaneous placement of a flexible sensor 12 (see FIG. 2), or the like, at a selected site in the body of a user. The implantable analyte sensor set 10 includes a hollow, slotted insertion needle 14, and a cannula 16. The needle 14 is used to facilitate quick and easy subcutaneous placement of the cannula 16 at the subcutaneous insertion site. The cannula 16 includes a sensing portion 18 of the sensor 12 to expose one or more sensor electrodes 20 to the user's bodily fluids through a window 22 formed in the cannula 16. After insertion, the insertion needle 14 is withdrawn to leave the cannula 16 with the sensing portion 18 and the sensor electrodes 20 in place at the selected insertion site.

In preferred embodiments, the implantable subcutaneous analyte sensor set 10 facilitates accurate placement of a flexible thin film electrochemical sensor 12 of the type used for monitoring specific blood parameters representative of a user's condition. Preferably, the sensor 12 monitors blood glucose levels, and may be used in conjunction with automated or semi-automated medication infusion pumps of the external or implantable type as described in U.S. Pat. Nos. 4,562,751; 4,678,408; 4,685,903 or 4,573,994, to deliver insulin to a diabetic patient. However, other embodiments may monitor other analytes to determine viral load, HIV activity, bacterial levels, cholesterol levels, medication levels, or the like.

Preferred embodiments of the flexible electrochemical sensor 12 are constructed in accordance with thin film mask techniques to include elongated thin film conductors embedded or encased between layers of a selected insulative material such as polyimide film or sheet. The sensor electrodes 20 at a tip end of the sensing portion 18 are exposed through one of the insulative layers for direct contact with patient blood, or other bodily fluids, when the sensor 12 is subcutaneously placed at an insertion site. The sensing portion 18 is joined to a connection portion 24 (see FIG. 2) that terminates in conductive contact pads, or the like, which are also exposed through one of the insulative layers. In alternative embodiments, other types of implantable analyte sensors, such as chemical based, optical based, or the like, may be used.

Figure 2:
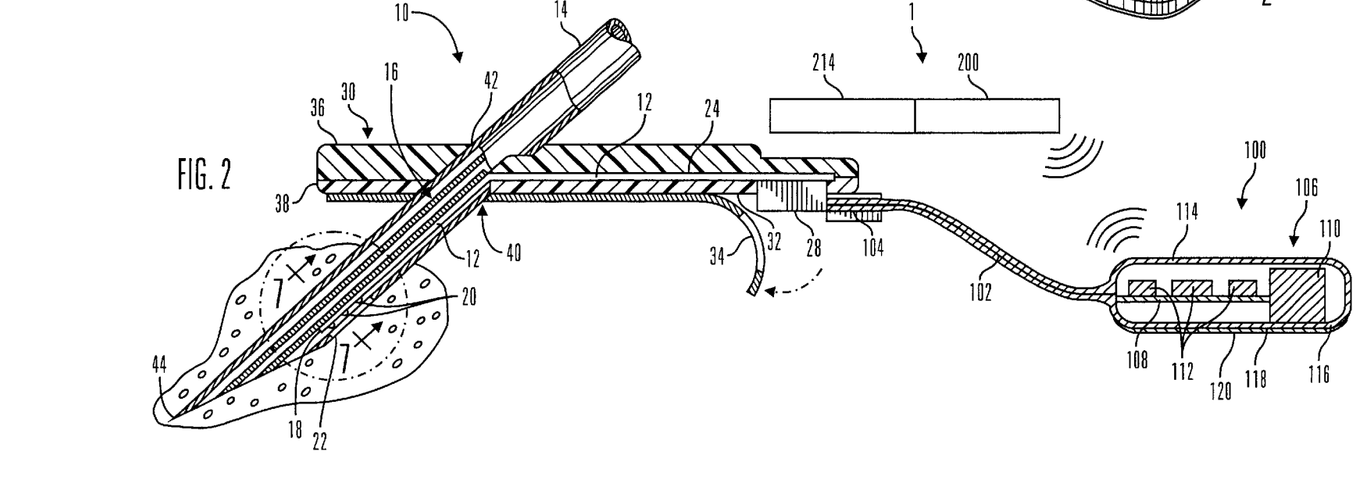
FIG. 2 is an enlarged longitudinal vertical section taken generally on the line 2—2 of FIG. 1.
Figure 3:
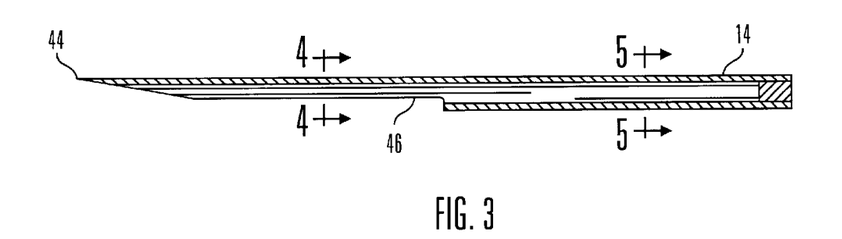
FIG. 3 is an enlarged longitudinal sectional of a slotted insertion needle used in the insertion set of FIGS. 1 and 2.
Figure 4:
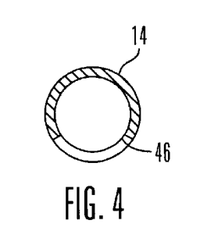
FIG. 4 is an enlarged transverse section taken generally on the line 4—4 of FIG. 3.
Figure 5:
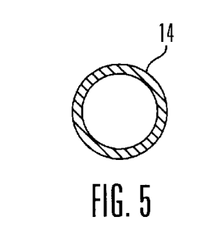
FIG. 5 is an enlarged transverse section taken generally on the line 5—5 of FIG. 3.

As is known in the art, and illustrated schematically in FIG. 2, the connection portion 24 and the contact pads are generally adapted for a direct wired electrical connection to a suitable sensor monitor for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 of the analyte sensor set 10 may be conveniently connected electrically to the sensor monitor (not shown), a Holter-type recorder 100, or a data processor 200, computer, communication station, or the like, by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 are configured or formed to work with either a wired or a wireless recording system.

Figure 1:
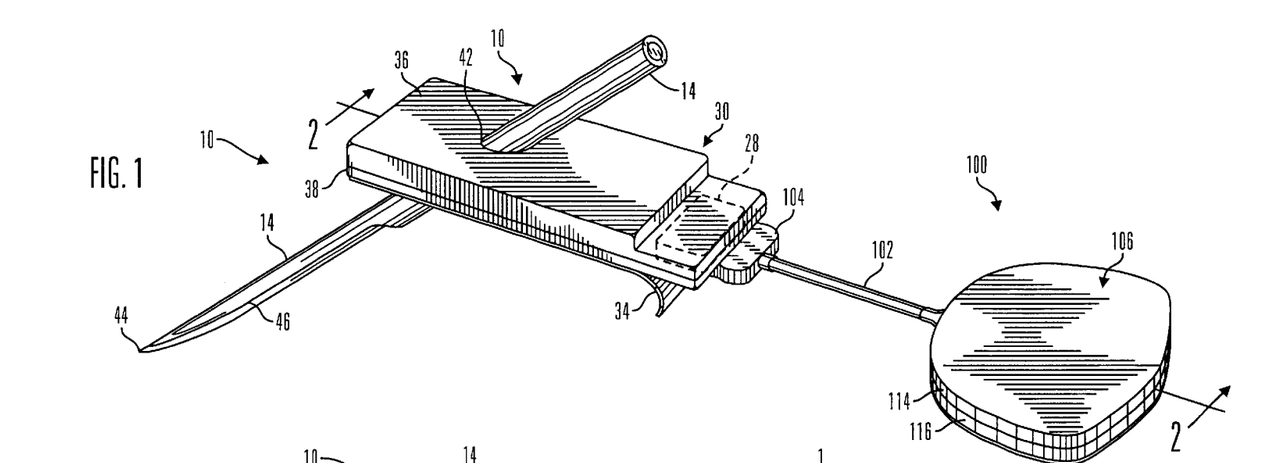
FIG. 1 is a is a perspective view illustrating a subcutaneous sensor insertion set and Holter-type monitor device embodying the novel features of the invention.

The sensor 12 is mounted in a mounting base 30 adapted for placement onto the skin of a user. As shown, the mounting base 30 is a generally rectangular pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the sensing portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In further alternative embodiments, the mounting base may be other shapes, such as circular, oval, hour-glass, butterfly or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a full round cross-sectional shape, and may be closed off at a rear end of the needle 14. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled 'DISPOSABLE SENSOR INSERTION ASSEMBLY," which are herein incorporated by reference.

Figure 6:
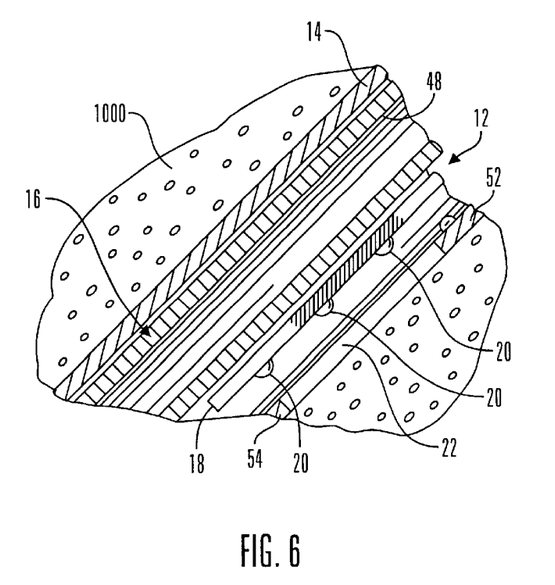
FIG. 6 is an enlarged fragmented sectional view corresponding generally with the encircled region 6 of FIG. 2.
Figure 7:
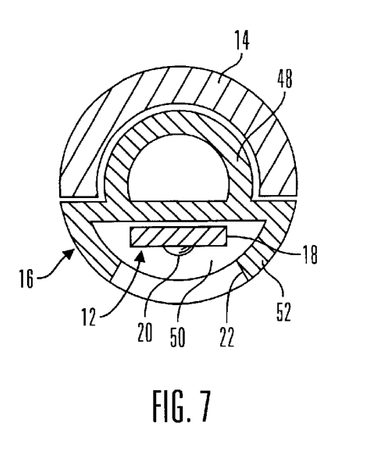
FIG. 7 is an enlarged transverse section taken generally on the line 7—7 of FIG. 2.

The cannula 16 is best shown in FIGS. 6 and 7, and includes a first portion 48 having partly-circular cross-section to fit within the insertion needle 14 that extends downwardly from the mounting base 30. In alternative embodiments, the first portion 48 may be formed with a solid core; rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guideably supporting the sensing portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates slightly before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed.

As shown in FIGS. 1 and 2, the Holter-type recorder 100 is coupled to a subcutaneous analyte sensor set 10 by a cable 102 through a connector 104 that is electrically coupled to the connector block 28 of the connector portion 24 of the subcutaneous analyte sensor set 10. In alternative embodiments, the cable 102 may be omitted, and the Holter-type recorder 100 may include an appropriate connector (not shown) for direct connection to the connector portion 24 of the subcutaneous analyte sensor set 10 or the subcutaneous analyte sensor set 10 may be modified to have the connector portion 24 positioned at a different location, such as for example, the top of the subcutaneous sensor set 10 to facilitate placement of the telemetered characteristic monitor transmitter over the subcutaneous sensor set 10. This would minimize the amount of skin surface covered or contacted by medical devices, and tend to minimize potential electrical interference induced by movement of the subcutaneous analyte sensor set 10 relative to the telemetered characteristic monitor transmitter 100. In further alternative embodiments, the cable 102 and the connector 104 may be formed as add-on adapters to fit different types of connectors on different types or kinds of sensor sets. The use of adapters would facilitate adaptation of the Holter-type recorder 100 to work with a wide variety of sensor systems.

The Holter-type recorder 100 includes a housing 106 that supports a printed circuit board 108, batteries 110, memory storage 112, and the cable 102 with the connector 104. In preferred embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In preferred embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In preferred embodiments, the housing 106 is disk or oval shaped. However, in alternative embodiments, other shapes, such as hour glass, rectangular or the like, may be used. Preferred embodiments of the housing 106 are sized in the range of 1.5 inches squared by 0.25 inches thick to minimize weight, discomfort and the noticeability of the Holter-type recorder 100 on the body of the user. However, larger or smaller sizes, such as 0.5 inches squared and 0.15 inches thick or less, and 3.0 inches squared and 0.5 inches thick or more, may be used.

As shown, the lower case 116 may have an underside surface coated with a suitable pressure sensitive adhesive layer 118, with a peel-off paper strip 120 normally provided to cover and protect the adhesive layer 118, until the Holter-type recorder 100 is ready for use. In preferred embodiments, the adhesive layer 118 includes an antibacterial agent to reduce the chance of infection; however, alternative embodiments may omit the agent. In further alternative embodiments, the adhesive layer 118 may be omitted and the Holter-type recorder 100 is secured to the body by other methods, such as an adhesive overdressing, straps, belts, clips or the like.

In preferred embodiments, the cable 102 and connector 104 are similar to (but not necessarily identical to) shortened versions of a cable and connector that are used to provide a standard wired connection between the subcutaneous analyte sensor set 10 and a sensor monitor. This allows the Holter-type recorder 100 to be used with existing subcutaneous analyte sensor sets 10, and avoids the necessity to re-certify the connector portion 24 of the subcutaneous analyte sensor set 10 for use with a Holter-type recorder 100.

The cable 102 should also include a flexible strain relief portion (not shown) to minimize strain on the subcutaneous sensor set 10 and prevent movement of the implanted sensor 12, which can lead to discomfort or dislodging of the analyte sensor set 10. The flexible strain relief portion is intended to minimize sensor artifacts generated by user movements that causes the subcutaneous analyte sensor set 10 to move relative to the Holter-type recorder 100.

The interface of the Holter-type recorder 100 connects with the cable 102 that is connected with the subcutaneous sensor set 10. In preferred embodiments, the sensor interface is permanently connected to the cable 102. However, in alternative embodiments, the sensor interface may be configured in the form of a jack to accept different types of cables that provide adaptability of the Holter-type recorder 100 to work with different types of subcutaneous analyte sensors and/or analyte sensors placed in different locations of the user's body. In preferred embodiments, the printed circuit board 108, and associated electronics, are capable of operating in a temperature range of 0° C. and 50° C. However, larger or smaller temperature ranges may be used.

Preferably, the battery assembly will use a weld tab design to connect power to the system. For example, it can use three series silver oxide 357 battery cells 110, or the like. However, it is understood that different battery chemistries may be used, such as lithium, alkaline or the like, and different numbers of batteries can be used. In further embodiments, the sensor interface will include circuitry and/or a mechanism for detecting connection to the subcutaneous analyte sensor set 10. This would provide the capability to save power and to more quickly and efficiently start initialization of the subcutaneous analyte sensor set 10. In preferred embodiments, the batteries 110 have a life in the range of 2 weeks to 2 years, and provide a low battery warning alarm. Alternative embodiments may provide longer or shorter battery lifetimes, or include a power port or solar cells to permit recharging of the batteries 110 in the Holter-type recorder 100.

In preferred embodiments, the Holter-type recorder 100 provides power, through the cable 102 and cable connector 104 to the analyte sensor set 10. The power is used to drive the analyte sensor set 10. The power connection is also used to speed the initialization of the sensor 12, when it is first placed under the skin. The use of an initialization process can reduce the time for sensor 12 stabilization from several hours to an hour or less. The preferred initialization procedure uses a two step process. First, a high voltage (preferably between 1.0–1.2 volts—although other voltages may be used) is applied to the sensor 12 for 1 to 2 minutes (although different time periods may be used) to allow the sensor 12 to stabilize. Then, a lower voltage (preferably between 0.5–0.6 volts—although other voltages may be used) is applied for the remainder of the initialization process (typically 58 minutes or less). Other stabilization/initialization procedures using differing currents, currents and voltages, different numbers of steps, or the like, may be used. Other embodiments may omit the initialization/stabilization process, if not required by the analyte sensor or if timing is not a factor.

At the completion of the stabilizing process, an initial reading may be downloaded from the analyte sensor set 10 and the Holter-type recorder 100 to the data processor 200, computer, communication station, or the like, to verify proper operation of the analyte sensor 10 and the Holter-type recorder 100. In alternative embodiments, a fluid containing a known value of glucose may be injected into the site around the analyte sensor set 10, and then the Holter-type recorder 100 records the data for the known value to provide a reference point to the recorded data. During the calibration process, the Holter-type recorder 100 checks to determine if the analyte sensor set 10 is still connected. If the analyte sensor set 10 is no longer connected, the Holter-type recorder 100 will abort the stabilization process and sound an alarm (or flash a light, or download a signal to the data processor 200, computer, communication station, or the like, to sound an alarm).

Additional embodiments of the Holter-type recording device may include an alarm, such as a piezo element, or the like, that will notify of an alarm or error condition. The piezo element may also be used to transmit data by hyper-audio frequencies.

In further alternative embodiments, the Holter-type recorder 100 can be combined with a analyte sensor set 10 as a single unit. This would be particularly well adapted where batteries and the recorder can be made cheaply enough to facilitate changing the Holter-type recorder 100 with each new analyte sensor set 10.

As shown in FIG. 2, the data processor 200, computer, communication station, or the like, may include a display 214 that is used to display the results of the measurement received from the sensing portion 18 in the analyte sensor set 10 received via a download from the Holter-type recorder 100. The results and information displayed includes, but is not limited to, trending information of the characteristic (e.g., rate of change of glucose), graphs of historical data, average characteristic levels (e.g., glucose), or the like. The display may be used to show glucose meter (or calibration) data. Alternative embodiments include the ability to scroll through the data. The display 214 may also be used with buttons (not shown) on the data processor 200, computer, communication station, or the like, characteristic monitor to program or update data in the data processor 200.

In further embodiments of the present invention, the data processor 200, computer, communication station, or the like, may be replaced by a different device. For example, in one embodiment, the Holter-type recorder 100 communicates with an RF programmer (not shown) that is also used to program and obtain data from an infusion pump or the like. The RF programmer may also be used to update and program the recorder 100, if the recorder 100 includes a receiver for remote programming, calibration or data receipt. The RF programmer can be used to store data obtained from the sensing portion 18 and then provide it to either an infusion pump, characteristic monitor, computer or the like for analysis. In further embodiments, the recorder 100 may transmit the data to a medication delivery device, such as an infusion pump or the like, as part of a closed loop system. This would allow the medication delivery device to compare sensor results with medication delivery data and either sound alarms when appropriate or suggest corrections to the medication delivery regimen. In preferred embodiments, the recorder 100 would include a transmitter to receive updates or requests for additional sensor data. An example of one type of RF programmer can be found in U.S. patent application Ser. No. 60/096,994 filed Aug. 18, 1998 and is entitled "INFUSION DEVICE WITH REMOTE PROGRAMMING, CARBOHYDRATE CALCULATOR AND/OR VIBRATION ALARM CAPABILITIES," which is herein incorporated by reference.

In use, the implantable analyte sensor set 10 permits quick and easy subcutaneous placement of the sensing portion 18 at a selected site within the body of the user. More specifically, the peel-off strip 34 (see FIG. 1) is removed from the mounting base 30, at which time the mounting base 30 can be pressed onto and seated upon the patient's skin. During this step, the insertion needle 14 pierces the user's skin and carries the protective cannula 16 with the sensing portion 18 to the appropriate subcutaneous placement site. During insertion, the cannula 16 provides a stable support and guide structure to carry the flexible sensor 12 to the desired placement site. When the sensor 12 is subcutaneously placed, with the mounting base 30 seated upon the user's skin, the insertion needle 14 can be slidably withdrawn from the user. During this withdrawal step, the insertion needle 14 slides over the first portion 48 of the protective cannula 16, leaving the sensing portion 18 with electrodes 20 directly exposed to the user's bodily fluids via the window 22. Further description of the needle 14 and the sensor set 10 are found in U.S. Pat. No. 5,586,553, entitled "TRANSCUTANEOUS SENSOR INSERTION SET"; co-pending U.S. patent application Ser. No. 08/871,831, entitled 'DISPOSABLE SENSOR INSERTION ASSEMBLY"; and co-pending U.S. patent application Ser. No. 09/161,128, filed Sep. 25, 1998, entitled "A SUBCUTANEOUS IMPLANTABLE SENSOR SET HAVING THE CAPABILITY TO REMOVE OR DELIVER FLUIDS TO AN INSERTION SITE," which are herein incorporated by reference.

Next, the user connects the connection portion 24 of the sensor set 10 to the cable 102 of the Holter-type recorder 100, so that the sensor 12 can then be used over a prolonged period of time for taking blood chemistry or characteristic readings, such as blood glucose readings in a diabetic patient. Preferred embodiments of the Holter-type recorder 100 detect the connection of the sensor 12 to activate the Holter-type recorder 100. For instance, connection of the sensor 12 may activate a switch or close a circuit to turn the Holter-type recorder 100 on. The use of a connection detection provides the capability to maximize the battery and shelf life of the Holter-type recorder prior to use, such as during manufacturing, test and storage. Alternative embodiments of the present invention may utilize an on/off switch (or button) on the Holter-type recorder 100.

The recorder 100 is then affixed to the user's body with an adhesive overdressing. Alternatively, the peel-off strip 34 (see FIG. 1) is removed from the lower case 116, at which time the lower case 116 can be pressed onto and seated upon the patient's skin. The user then activates the recorder 100, or the recorder is activated by detection of the connection to the sensor 12 of the analyte sensor set 10. Generally, the act of connecting (and disconnecting) the sensor 12 activates (and deactivates) the Holter-type recorder 100, and no other interface is required. In alternative steps, the analyte sensor set 10 is connected to the recorder 100 prior to placement of the sensor 12 to avoid possible movement or dislodging of the sensor 12 during attachment of the recorder 100. Also, the recorder may be attached to the user prior to attaching the sensor set 10 to the recorder 100.

The user then verifies proper operation of the recorder 100. Thus, once a user attaches a recorder 100 to an analyte sensor set 10, the sensor 12 is automatically initialized and readings are periodically recorded, together with other information, in the Holter-type recorder 100.

After an analyte sensor set 10 has been used for a period of time, it is replaced. The user will disconnect the analyte sensor set 10 from the cable 102 of the Holter-type recorder 100. In preferred embodiments, if additional measurements are required and/or desired, the Holter-type recorder 100 is removed and positioned adjacent the new site for a new analyte sensor set 10. In alternative embodiments, the user does not need to remove the recorder 100. A new analyte sensor set 10 and sensor 12 are attached to the Holter-type recorder 100 and connected to the user's body. Recording then continues, as with the previous sensor 12. If the user must replace the Holter-type recorder 100, the user disconnects the Holter-type recorder 100 from the analyte sensor set 10 and the user's body. Finally, the data stored in the memory 112 of the Holter-type recorder 100 is downloaded (or transmitted) to the data processor 200, computer, communication station, or the like, for analysis and review.

Additional embodiments of the present invention may include a vibrator alarm (or optical indicator such as an L.E.D.) in the Holter-type recorder 100 to provide a tactile (vibration) alarm to the user, so as to indicate an analyte sensor set 10 malfunction, improper connection, low battery, missed message, bad data, interference, or the like. The use of a vibration alarm provides additional reminders to an audio alarm, which could be important with someone suffering an acute reaction, or to have non-audio alarms to preserve and conceal the presence of the Holter-type recorder 100.

Figure 8:
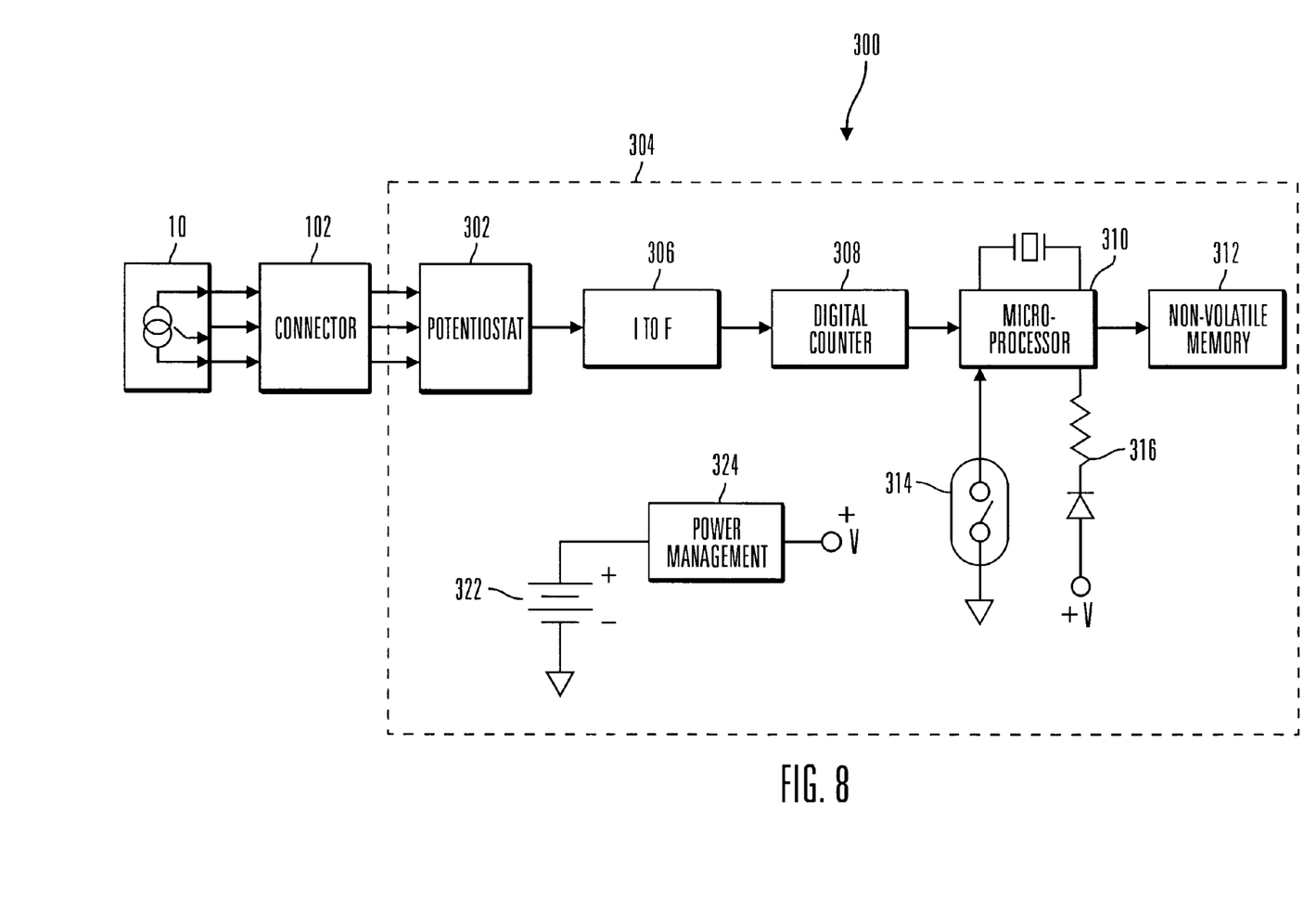
FIG. 8 is a simplified block diagram of a Holter-type monitoring device in accordance with an embodiment of the present invention.
Figure 9:
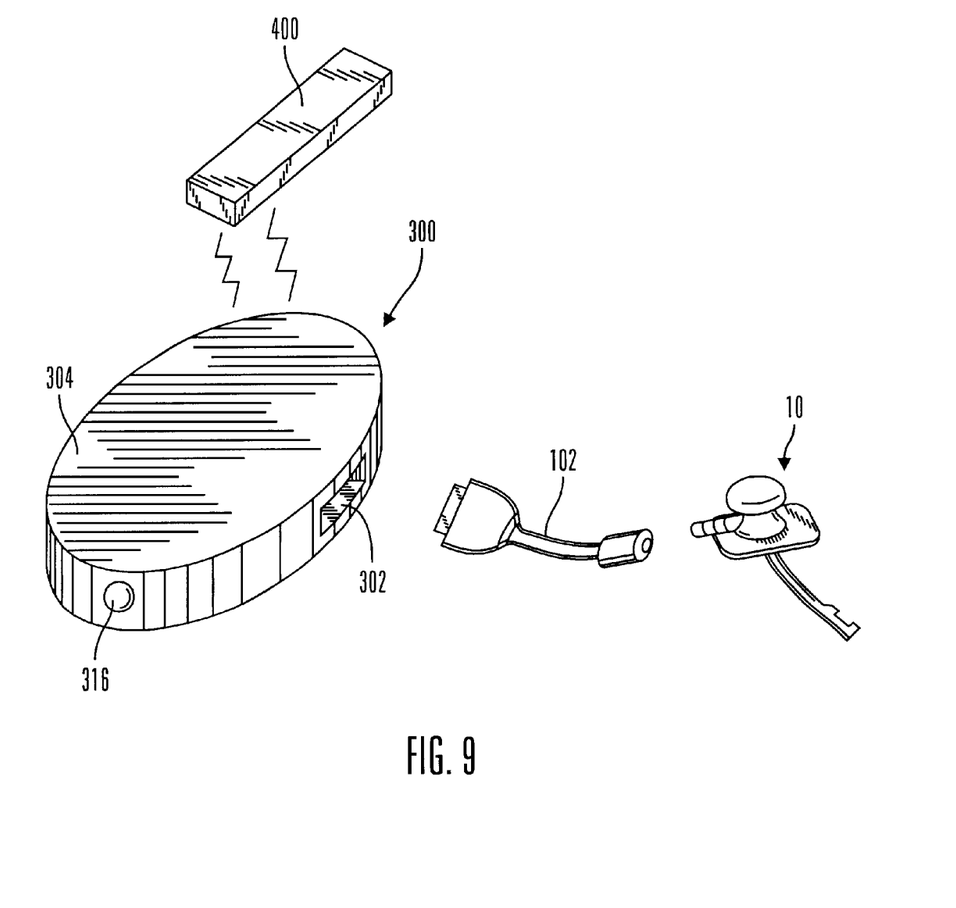
FIG. 9 is a perspective view of a Holter-type monitor device and a download activation device in accordance the embodiment shown in FIG. 8.

FIGS. 8 and 9 show a Holter-type recorder 300 in accordance with another embodiment of the present invention. In the illustrated embodiment, the analyte sensor 10 is connected, via a cable (or connector) 102, to a signal conditioning circuit 302, such as a potentiostat or the like, in a housing 304 of the Holter-type recorder 300. The signal conditioning circuit 302 is in turn connected to a current to frequency converter (I to F) 306. The output of the I to F 306 is a digital frequency that varies as a function of the sensor signal produced by the analyte sensor 10. In alternative embodiments, other signals, such as voltage, or the like, may be converted to frequency. The digital frequency is then counted by a digital counter, and the digital counter 310 value is periodically read and stored with an indication of relative time, by a microprocessor 310, into a non-volatile memory 312. When the monitoring period is over, the data is downloaded from the Holter-type recorder 300 by activating a reed switch 314. In preferred embodiments, the reed switch 314 is activated by a magnet 400 (see FIG. 9). However, in alternative embodiments, a stylus activated switch, a code transmitted to the Holter-type recorder, a manual switch, or the like, may be used. Once the reed switch 314 is closed, the Holter-type recorder 300 begins downloading the stored data by driving an LED 316 at a data rate until all of the stored data and relative time indications are transmitted to a receiver and processing device, such as a computer, laptop, PC, communication station, or the like. In alternative embodiments, a wired connection, ultrasonic frequencies, optical, RF or other transmission protocol may be used. In preferred embodiments, the stored data is maintained in the non-volatile memory 312 until confirmation of the successful download is received by the Holter-type recorder 300. In alternative embodiments, an additional switch must be activated to delete the stored data, or the Holter-type recorder is cleared using an on-board program that clears the memory after a predetermined period of time. The Holter-type recorder 300 also includes a power source 322 and a power management circuit 324 to power the Holter-type recorder 300.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A Holter-type monitor system for monitoring a glucose characteristic of a user, the system comprising:
    a remotely located data receiving device;
    an analyte sensor for measuring glucose in interstitial fluid and for producing a signal indicative of the glucose characteristic of the user; and
    a Holter-type recording device including:
        a housing;
        a sensor connector coupled to the housing and that is connectable to the analyte sensor to receive the produced signals from the analyte sensor;
        a processor including a memory coupled to the sensor connector to store the signals from the analyte sensor for delivery to the remotely located data receiving device; and
        data downloading means coupled to the processor for downloading the stored signals to the remotely located data receiving device, wherein the Holter-type recording device initializes the analyte sensor when the analyte sensor is connected to the Holter-type recording device.

2. A Holter-type monitor system according to claim 1, wherein the Holter-type recording device downloads the stored signals via the data downloading means by radio frequencies.

3. A Holter-type monitor system according to claim 1, wherein the Holter-type recording device downloads the stored signals via the data downloading means by optical frequencies.

4. A Holter-type monitor system according to claim 1, wherein the analyte sensor is an implantable analyte sensor, and wherein the sensor connector of the Holter-type recording device includes a cable that is connectable to the implantable analyte sensor.

5. A Holter-type monitor system according to claim 4, wherein the implantable analyte sensor is configured for a direct wired connection to a characteristic monitor using a standardized connector, and wherein the sensor connector of the Holter-type recording device is formed to connect to the configured implantable analyte sensor using the standardized connector.

6. A Holter-type monitor system according to claim 1, wherein the analyte sensor is a percutaneous analyte sensor, and wherein the sensor connector of the Holter-type recording device includes a cable that is connected to the percutaneous analyte sensor.

7. A Holter-type monitor system according to claim 6, wherein the percutaneous analyte sensor is configured for a direct wired connection to a characteristic monitor using a standardized connector, and wherein the sensor connector of the Holter-type recording device is formed to connect to the configured percutaneous analyte sensor using the standardized connector.

8. A Holter-type monitor system according to claim 1, wherein the analyte sensor is an skin surface analyte sensor, and wherein the sensor connector of the Holter-type recording device includes a cable that is connectable to the skin surface analyte sensor.

9. A Holter-type monitor system according to claim 8, wherein the skin surface analyte sensor is configured for a direct wired connection to a characteristic monitor using a standardized connector, and wherein the sensor connector of the Holter-type recording device is formed to connect to the configured skin surface analyte sensor using the standardized connector.

10. A Holter-type monitor system according to claim 1, wherein the data receiving device is a data receiver that also provides data to another device.

11. A Holter-type monitor system according to claim 1, wherein the data receiving device is a characteristic monitor.

12. A Holter-type monitor system according to claim 1, wherein the sensor connector applies power to the analyte sensor.

13. A Holter-type monitor system according to claim 1, wherein the interstitial fluid for contact with the analyte sensor is obtained using invasive techniques.

14. A Holter-type monitor system according to claim 1, wherein the analyte sensor initialization includes using stabilization.

15. A Holter-type monitor system according to claim 1, wherein the analyte sensor initialization includes using calibration.

16. A Holter-type monitor system according to claim 1, wherein the analyte sensor is an enzyme based glucose sensor.

17. A Holter-type monitor system according to claim 1, wherein the Holter-type recording device includes an optical indicator.

18. A Holter-type monitor system for monitoring a glucose characteristic of a user, the system comprising:
 a remotely located data receiving device;
 an analyte sensor for measuring glucose in interstitial fluid for producing a signal indicative of the glucose characteristic of the user; and
 a Holter-type recording device including:
  a housing;
  a sensor connector coupled to the housing and that is connectable to the analyte sensor to receive the produced signals from the anayte sensor;
  a processor including a memory coupled to the sensor connector to store the signals from the analyte sensor for delivery to the remotely located data receiving device; and
  data downloading means coupled to the processor for downloading the stored signals to the remotely located data receiving device,
  wherein the Holter-type recording device further includes a receiver to receive data and instructions from the data receiving device, and
  wherein the Holter-type recording device initializes the analyte sensor when the analyte sensor is connected to the Holter-type recording device.

19. A Holter-type monitor system for monitoring a glucose characteristic of a user, the system comprising:
 a remotely located data receiving device;
 an analyte sensor for measuring glucose in interstitial fluid for producing a signal indicative of the glucose characteristic of the user; and
 a Holter-type recording device including:
  a housing;
  a sensor connector coupled to the housing and that is connectable to the analyte sensor to receive the produced signals from the analyte sensor;
  a processor including a memory coupled to the sensor connector to store the signals from the analyte sensor for delivery to the remotely located data receiving device; and
  data downloading means coupled to the processor for downloading the stored signals to the remotely located data receiving device,
  wherein the data receiving device is an RF programmer, and
  wherein the Holter-type recording device initializes the analyte sensor when the analyte sensor is connected to the Holter-type recording device.

20. A Holter-type monitor system for monitoring a glucose characteristic of a user, the system comprising:
 a remotely located data receiving device;
 an analyte sensor for measuring glucose in interstitial fluid for producing a signal indicative of the glucose characteristic of the user; and
 a Holter-type recording device including:
  a housing;
  a sensor connector coupled to the housing and that is connectable to the analyte sensor to receive the produced signals from the analyte sensor;
  a processor including a memory coupled to the sensor connector to store the signals from the analyte sensor for delivery to the remotely located data receiving device; and
  data downloading means coupled to the processor for downloading the stored signals to the remotely located data receiving device,
  wherein the data receiving device is a medication delivery device, and
  wherein the Holter-type recording device initializes the analyte sensor when the analyte sensor is connected to the Holter-type recording device.

21. A Holter-type monitor system for monitoring a glucose characteristic of a user, the system comprising:
 a remotely located data receiving device;
 an analyte sensor for measuring glucose in interstitial fluid for producing a signal indicative of the glucose characteristic of the user; and
 a Holter-type recording device including:
  a housing;
  a sensor connector coupled to the housing and that is connectable to the analyte sensor to receive the produced signals from the analyte sensor;
  a processor including a memory coupled to the sensor connector to store the signals from the analyte sensor for delivery to the remotely located data receiving device; and
  data downloading means coupled to the processor for downloading the stored signals to the remotely located data receiving device,
  wherein the data receiving device is an infusion pump, and
  wherein the Holter-type recording device initializes the analyte sensor when the analyte sensor is connected to the Holter-type recording device.

22. A Holter-type monitor system for monitoring a glucose characteristic of a user, the system comprising:
 a remotely located data receiving device;
 an analyte sensor for measuring glucose in interstitial fluid for producing a signal indicative of the glucose characteristic of the user; and
 a Holter-type recording device including:
  a housing;
  a sensor connector coupled to the housing and that is connectable to the analyte sensor to receive the produced signals from the analyte sensor;
  a processor including a memory coupled to the sensor connector to store the signals from the analyte sensor for delivery to the remotely located data receiving device; and data downloading means port coupled to the processor for downloading the stored signals to the remotely located data receiving device, and further including a separate glucose detection device to provide calibration data, and wherein all processed signals received by the data receiving device are post processed with the calibration date, and wherein the Holter-type recording device initializes the analyte sensor when the analyte sensor is connected to the Holter-type recording device.

23. A Holter-type recording device for use in a system with a remotely located data processing device and an analyte sensor for measuring glucose levels in interstitial fluid and for producing a signal indicative of a glucose characteristic of a user, the Holter-type recording device comprising:

a housing;

a sensor connector coupled to the housing and that is connectable to the analyte sensor to receive the produced signal from the analyte sensor;

a processor including a memory coupled to the sensor connector to store the signal from the analyte sensor for delivery to the remotely located data processing device; and data downloading means coupled to the processor for downloading the stored signals to the remotely located data processing device, wherein the Holter-type recording device initializes the analyte sensor when the analyte sensor is connected to the Holter-type recording device.

24. A Holter-type recording device according to claim 23, wherein the data downloading means downloads the stored signals via the data port by radio frequencies.

25. A Holter-type recording device according to claim 23, wherein the analyte sensor is an implantable analyte sensor, and wherein the sensor connector of the Holter-type recording device includes a cable that is connectable to the implantable analyte sensor.

26. A Holter-type recording device according to claim 25, wherein the implantable analyte sensor is configured for a direct wired connection to a characteristic monitor using a standardized connector, and wherein the sensor connector of the Holter-type recording device is formed to connect to the configured implantable analyte sensor using the standardized connector.

27. A Holter-type recording device according to claim 23, wherein the analyte sensor is a percutaneous analyte sensor, and wherein the sensor connector of the Holter-type recording device includes a cable that is connectable to the percutaneous analyte sensor.

28. A Holter-type recording device according to claim 27, wherein the percutaneous analyte sensor is configured for a direct wired connection to a characteristic monitor using a standardized connector, and wherein the sensor connector of the Holter-type recording device is formed to connect to the configured percutaneous analyte sensor using the standardized connector.

29. A Holter-type recording device according to claim 23, wherein the analyte sensor is an skin surface analyte sensor, and wherein the sensor connector of the Holter-type recording device includes a cable that is connectable to the skin surface analyte sensor.

30. A Holter-type recording device according to claim 29, wherein the skin surface analyte sensor is configured for a direct wired connection to a characteristic monitor using a standardized connector, and wherein the sensor connector of the Holter-type recording device is formed to connect to the configured skin surface analyte sensor using the standardized connector.

31. A Holter-type recording device according to claim 23, further including a receiver to receive data and instructions from the data processing device.

32. A Holter-type recording device according to claim 23, wherein the housing includes a bio-compatible adhesive adapted to secure the housing to a skin surface of the user.

33. A Holter-type recording device according to claim 32, wherein the bio-compatible adhesive is an anti-bacterial adhesive.

34. A Holter-type recording device according to claim 23, wherein the housing is secured to a skin surface of the user by an adhesive overdressing.

35. A Holter-type recording device according to claim 23, wherein the housing is less than about 1.5 inches in diameter by 0.25 inches thick.

36. A Holter-type recording device according to claim 23, wherein the housing is resistant to fluids when immersed in a fluid.

37. A Holter-type recording device according to claim 23, wherein the Holter-type recording device is operable in a temperature range of 0° C. to 50° C.

38. A Holter-type recording device according to claim 23, wherein the Holter-type recording device includes a power source that has an operable life of at least 2 weeks.

39. A Holter-type recording device according to claim 23, wherein the sensor connector applies power to the analyte sensor.

40. A Holter-type recording device according to claim 23, wherein the Holter-type recording device is activated by detection of a connection of the analyte sensor to the sensor connector.

41. A Holter-type recording device according to claim 23, wherein the Holter-type recording device includes an optical indicator.

* * * * *